(12) United States Patent
Planard-Luong et al.

(10) Patent No.: US 11,510,477 B2
(45) Date of Patent: Nov. 29, 2022

(54) DEVICE FOR TREATING HUMAN KERATINOUS MATERIAL, IN PARTICULAR WITH THE AID OF AN ELECTRIC CURRENT

(71) Applicants: L'OREAL, Paris (FR); SEB S.A., Ecully (FR)

(72) Inventors: Thi Hong Lien Planard-Luong, Chevilly Larue (FR); Franck Mandica, Francheville (FR); Helene Pernot, Lyons (FR); Johan Sabattier, Mornant (FR)

(73) Assignees: L'OREAL, Paris (FR); SEB S.A., Ecully (FR)

( * ) Notice: Subject to any disclaimer, the term of this patent is extended or adjusted under 35 U.S.C. 154(b) by 100 days.

(21) Appl. No.: 16/061,875

(22) PCT Filed: Dec. 6, 2016

(86) PCT No.: PCT/EP2016/079911
§ 371 (c)(1),
(2) Date: Jun. 13, 2018

(87) PCT Pub. No.: WO2017/102446
PCT Pub. Date: Jun. 22, 2017

(65) Prior Publication Data
US 2018/0368552 A1 Dec. 27, 2018

(30) Foreign Application Priority Data
Dec. 17, 2015 (FR) ...................................... 1562621

(51) Int. Cl.
*A45D 34/00* (2006.01)
*A45D 34/04* (2006.01)
(Continued)

(52) U.S. Cl.
CPC ......... *A45D 34/041* (2013.01); *A61N 1/0432* (2013.01); *A61N 1/0472* (2013.01);
(Continued)

(58) Field of Classification Search
CPC ...... A61N 1/0428; A61N 1/0448; A61N 1/26; A61N 1/322; A61N 1/325; A61N 1/30;
(Continued)

(56) References Cited

U.S. PATENT DOCUMENTS 4,858,600 A    8/1989  Gross et al.
5,090,402 A    2/1992  Bazin et al.
(Continued)

FOREIGN PATENT DOCUMENTS

CN    1313213 C      5/2007
CN    101020513 A    8/2007
(Continued)

OTHER PUBLICATIONS

Japanese Office Action for JP2018-531659 dated Jun. 21, 2019 with English Translation (10 pages).
(Continued)

*Primary Examiner* — Nathan R Price
*Assistant Examiner* — Tania Ismail
(74) *Attorney, Agent, or Firm* — Shumaker, Loop & Kendrick, LLP (57) ABSTRACT

A device for treating human keratinous material, in particular with the aid of an electric current. The device includes a reservoir containing a composition, in particular cosmetic or dermatological, to be applied to the keratinous material, and an end fitting for the application of the composition contained in the reservoir, the end fitting comprising a plurality of application members and a distributor. The distributor includes at least one storage cavity for the composition and supply orifices to conduct the composition from the storage
(Continued)

cavity or cavities to the application members, and the distributor being configured so that the flow rate of the composition arriving at the application members is identical to within 20% for at least two application members, better for each application member.

17 Claims, 9 Drawing Sheets

(51) Int. Cl.
| | | |
|---|---|---|
| A61N 1/04 | (2006.01) | |
| A61H 7/00 | (2006.01) | |
| A61N 1/30 | (2006.01) | |
| A61N 1/32 | (2006.01) | |
| A61H 15/00 | (2006.01) | |
| A61H 15/02 | (2006.01) | |
| A61N 1/26 | (2006.01) | |
| A45D 40/00 | (2006.01) | |
| A45D 40/26 | (2006.01) | |
| A61M 37/00 | (2006.01) | |
| A61M 35/00 | (2006.01) | |
| A61M 25/00 | (2006.01) | |

(52) U.S. Cl.
CPC ........ *A45D 40/0075* (2013.01); *A45D 40/261* (2013.01); *A45D 2034/005* (2013.01); *A45D 2200/202* (2013.01); *A61H 7/003* (2013.01); *A61H 15/0078* (2013.01); *A61H 15/0085* (2013.01); *A61H 15/02* (2013.01); *A61H 2015/005* (2013.01); *A61H 2015/0007* (2013.01); *A61H 2015/0014* (2013.01); *A61H 2015/0042* (2013.01); *A61H 2015/0064* (2013.01); *A61H 2201/10* (2013.01); *A61K 2800/874* (2013.01); *A61M 25/003* (2013.01); *A61M 35/00* (2013.01); *A61M 2037/0007* (2013.01); *A61N 1/0428* (2013.01); *A61N 1/0448* (2013.01); *A61N 1/26* (2013.01); *A61N 1/30* (2013.01); *A61N 1/303* (2013.01); *A61N 1/322* (2013.01); *A61N 1/325* (2013.01); *A61N 1/327* (2013.01)

(58) Field of Classification Search
CPC ............. A61N 1/303; A61N 1/327; A61H 2015/0007; A61H 2015/0014; A61H 2015/0042; A61H 2015/005; A61H 2015/0064; A61H 15/0078; A61H 15/0085; A61H 15/02; A61H 2201/10; A61H 2201/1058; A61H 2201/1267; A61H 7/003; A61M 25/003; A61M 35/00; A61M 35/003; A61M 2037/0007; A45D 34/041; A45D 2034/005; A45D 40/0075; A45D 40/261; A45D 19/028; A61K 2800/874
See application file for complete search history.

(56) References Cited

U.S. PATENT DOCUMENTS

| 5,131,384 | A | 7/1992 | Obagi |
|---|---|---|---|
| 6,535,761 | B2 | 3/2003 | Bernabei |
| 6,947,791 | B2 | 9/2005 | Zhang et al. |
| 7,775,735 | B2 | 8/2010 | Habatjou |
| 10,946,191 | B2 * | 3/2021 | Cazares Delgadillo ................... A61N 1/303 |
| 2005/0107832 | A1 | 5/2005 | Bernabei |
| 2005/0209538 | A1 | 9/2005 | Lev et al. |
| 2006/0076361 | A1 | 4/2006 | Rueschhoff et al. |
| 2008/0200861 | A1 * | 8/2008 | Shalev ..................... A61Q 9/04 604/20 |
| 2010/0217176 | A1 | 8/2010 | Carrara et al. |
| 2010/0274329 | A1 | 10/2010 | Bradley et al. |
| 2012/0109041 | A1 | 5/2012 | Munz |
| 2012/0121309 | A1 * | 5/2012 | Liu ..................... A61H 15/0085 401/6 |
| 2013/0204178 | A1 | 8/2013 | Luzon et al. |
| 2013/0264358 | A1 | 10/2013 | Fallat, II et al. |
| 2015/0190074 | A1 | 7/2015 | McRae |

FOREIGN PATENT DOCUMENTS

| CN | 101532190 | A | 9/2009 | |
|---|---|---|---|---|
| CN | 103249339 | A | 8/2013 | |
| CN | 203777287 | U | 8/2014 | |
| EP | 1885217 | A2 | 2/2008 | |
| FR | 2619308 | A1 | 2/1989 | |
| FR | 2917299 | A1 | 12/2008 | |
| FR | 3015300 | A1 | 6/2015 | |
| GB | 2372705 | A * | 9/2002 | ............... A61N 1/30 |
| JP | S48108873 | U | 12/1973 | |
| JP | H01135015 | U | 9/1989 | |
| JP | H0271742 | A | 3/1990 | |
| JP | 2002369985 | A | 12/2002 | |
| JP | 2009-179915 | A1 | 8/2009 | |
| JP | 2011502656 | A | 1/2011 | |
| JP | 2013544282 | A | 12/2013 | |
| JP | 2015510419 | A | 4/2015 | |
| RU | 2270041 | C2 | 2/2006 | |
| RU | 2010123941 | A | 12/2011 | |
| WO | 2006130643 | A2 | 5/2006 | |
| WO | 2008/057640 | A2 | 5/2008 | |
| WO | 2010111997 | A2 | 10/2010 | |
| WO | 2013118114 | A1 | 8/2013 | |
| WO | 2014/180555 | A1 | 11/2014 | |
| WO | 2014180555 | A1 | 11/2014 | |
| WO | 2014/207750 | A1 | 12/2014 | |
| WO | 2015/091044 | A1 | 6/2015 | |
| WO | 2015091044 | A1 | 6/2015 | |
| WO | 2015097624 | A1 | 7/2015 | |

OTHER PUBLICATIONS

Japanese Office Action for JP2018-531657 dated Jul. 1, 2019 with English Translation (11 pages).
Japanese Office Action for JP2018-531653 dated Jul. 29, 2019 with English Translation (12 pages).
Japanese Office Action for JP2018-531626 dated Aug. 5, 2019 with English Translation (8 pages).
Japanese Office Action for JP2018-531627 dated Jun. 3, 2019 with English Translation (7 pages).
Non-Final Office Action in U.S. Appl. No. 16/062,209 dated Feb. 20, 2020.
Non-Final Office Action in U.S. Appl. No. 16/062,183 dated Feb. 20, 2020.
Russian Office Action of substantive examination for RU Application No. 2018121971/14 dated Mar. 18, 2019; 13 pages (includes English Translation).
Russian Office Action of Substantive Examination for RU Application No. 2018121748/14 (034416) dated Apr. 2, 2019 with English Translation (10 pages).
Russian Office Action of Substantive Examination for RU Application No. 2018121755/14 (034427) dated Apr. 2, 2019 with English Translation (10 pages).
Russian Office Action of Substantive Examination for RU Application No. 2018121754/14 (034423) dated Apr. 2, 2019 with English Translation (8 pages).
International Search Report dated Mar. 21, 2017 in International Patent Application No. PCT/EP2016/079911 (3 pages).
Written Opinion dated Mar. 21, 2017 in International Patent Application No. PCT/EP2016/079911 (5 pages).
International Preliminary Report on Patentability dated Jun. 19, 2018 in International Patent Application No. PCT/EP2016/079911 (6 pages).

(56) References Cited

OTHER PUBLICATIONS

International Search Report dated Mar. 21, 2017 in International Patent Application No. PCT/EP2016/079915 (3 pages).
Written Opinion dated Mar. 21, 2017 in International Patent Application No. PCT/EP2016/079915 (5 pages).
International Preliminary Report on Patentability dated Jun. 19, 2018 in International Patent Application No. PCT/EP2016/079915 (6 pages).
International Search Report dated Mar. 21, 2017 in International Patent Application No. PCT/EP2016/079923 (3 pages).
Written Opinion dated Mar. 21, 2017 in International Patent Application No. PCT/EP2016/079923 (5 pages).
International Preliminary Report on Patentability dated Jun. 19, 2018 in International Patent Application No. PCT/EP2016/079923 (6 pages).
International Search Report dated Feb. 24, 2017 in International Patent Application No. PCT/EP2016/079927 (3 pages).
Written Opinion dated Feb. 24, 2017 in International Patent Application No. PCT/EP2016/079927 (5 pages).
International Preliminary Report on Patentability dated Jun. 19, 2018 in International Patent Application No. PCT/EP2016/079927 (6 pages).
International Search Report dated Mar. 24, 2017 in International Patent Application No. PCT/EP2016/079922 (3 pages).
Written Opinion International Search Report dated Mar. 24, 2017 in International Patent Application No. PCT/EP2016/079922 (5 pages).
International Preliminary Report on Patentability dated Jun. 19, 2018 in International Patent Application No. PCT/EP2016/079922 (6 pages).
U.S. Appl. No. 16/062,183, filed Jun. 14, 2018.
U.S. Appl. No. 16/062,209, filed Jun. 14, 2018.
U.S. Appl. No. 16/062,913, filed Jun. 15, 2018.
U.S. Appl. No. 16/062,924, filed Jun. 15, 2018.
First Office Action for CN Patent App. No. 201680074289.9 with English Translation dated Jul. 3, 2020 (12 pages).
Non-Final Office Action in U.S. Appl. No. 16/062,913, dated Apr. 1, 2020.
Final Rejection for U.S. Appl. No. 16/062,209 dated Jun. 24, 2020 (12 pages).
Final Rejection for U.S. Appl. No. 16/062,913 dated Jun. 25, 2020 (8 pages).
Korean Office Action for Korean Pat. App. No. 10-2018-7017071 dated Jun. 20, 2020 (10 pages).
Non-Final Office Action for U.S. Appl. No. 16/062,924 dated Aug. 5, 2020 (11 pages).
Final Rejection for U.S. Appl. No. 16/062,183 dated Aug. 13, 2020 (13 pages).
Non-Final Office Action for U.S. Appl. No. 16/062,209 dated Nov. 9, 2020 (10 pages).
Non-Final Rejection for U.S. Appl. No. 16/062,913, dated Dec. 31, 2020 (9 pages).
English Translation of First Office Action for Chinese Pat. Application No. 201680074631.5, dated Apr. 9, 2021 (6 pages).
Non-Final Office Action for U.S. Appl. No. 16/062,209, dated May 26, 2021 (9 pages).
Corrected Notice of Allowability for U.S. Appl. No. 16/062,924, dated May 24, 2021 (7 pages).
Notice of Allowance for U.S. Appl. No. 16/062,924, dated Mar. 30, 2021 (10 pages).
Notice of Allowance for U.S. Appl. No. 16/062,913, dated May 13, 2021 (8 pages).
Final Rejection for U.S. Appl. No. 16/062,209, dated Sep. 27, 2021 (12 pages).

\* cited by examiner

DEVICE FOR TREATING HUMAN KERATINOUS MATERIAL, IN PARTICULAR WITH THE AID OF AN ELECTRIC CURRENT

BACKGROUND

The present invention relates to devices intended to carry out a treatment, in particular cosmetic or dermatological, of keratinous material, in particular of the skin, of the scalp, or of the hair. By "cosmetic or dermatological composition" is meant any composition such as defined in Directive 93/35/CEE of the Council of Jun. 14 1993.

The invention relates in particular to devices for the treatment, in particular cosmetic or dermatological, of keratinous material with the aid of an electric current.

It is known that the application of an electric current to the skin may facilitate the penetration of an active agent. It is thus known to treat human keratinous material with the aid of iontophoresis devices. Iontophoresis allows the diffusion of active agents through the skin by virtue of an electrical stimulation in a non-invasive manner. The current administered may be adjustable in terms of intensity and polarity (anodic or cathodic current). The transcutaneous diffusion of the molecules via iontophoresis is based on two principles, namely electro repulsion and electro-osmosis.

Electro repulsion is the migration of an ionized molecule by repulsion of charge of the same sign. Thus, a positively charged substance will diffuse through the skin at the level of the anode (+).

Electro-osmosis is the migration of a molecule, even non-ionized, by entrainment related to the stream of water from the anode to the cathode during iontophoresis. Under the effect of a current, the dissolved substances are entrained by the water or a solvent during migration.

Patent U.S. Pat. No. 5,090,402 pertains to an electric current applicator also exhibiting a massaging function, comprising a plurality of balls, all the balls being immersed in the composition reservoir which extends under a support of the balls.

The subject of patent U.S. Pat. No. 5,131,384 is a massaging applicator comprising a plurality of balls, including a central ball supplied directly with product. This massaging applicator is devoid of a system for applying an electric current.

In application US 2005/0107832, the applicator comprises a matrix of electrodes and is devoid of conducting pieces intended for distributing the composition.

SUMMARY

A need exists to further enhance the devices which facilitate the penetration of active agents through the skin so as to increase the efficacy of the iontophoresis.

A need exists in particular to benefit from a device for the treatment, in particular cosmetic or dermatological, of keratinous material, in particular with the aid of an electric current, which exhibits good efficacy and may be used with comfort and in complete safety.

The subject of the invention is thus, according to one of its aspects, a device for the treatment, in particular cosmetic or dermatological, of human keratinous material, with the aid of an electric current, comprising at least:

a reservoir containing a composition P, in particular cosmetic or dermatological, to be applied to the keratinous material, and an end fitting for the application of the composition contained in the reservoir, the end fitting comprising a plurality of application members and a distributor, the distributor comprising at least one storage cavity for the composition and supply orifices to conduct the composition from the storage cavity or cavities to the application members, the distributor being configured so that the flow rate of the composition arriving at the application members is identical to within 20%, better to within 15%, still better to within 10%, for at least two application members, better for each application member.

The flow rate of the composition arriving at the application members is the flow rate of the composition exiting the supply orifice corresponding to the application member in question, to supply the housing of said application member.

Two flow rates $D_1$ and $D_2$ are compared in the following way. $D_1$ being the lowest flow rate of the two, and $D_2$ highest flow rate of the two, the following ratio is calculated: $(D_2-D_1)/D_2$.

By "human keratinous material" is meant mainly the skin, in particular of the body or of the face, or else the scalp, the nails or the hair.

At least two supply orifices may have different cross sections, to compensate at least partly for the difference in the length of the path traversed by the composition to arrive at the corresponding housings.

The subject of the invention is further, according to another of its aspects, independently or in combination with the foregoing, a device for treatment, in particular cosmetic or dermatological, of human keratinous material, with the aid of an electric current, comprising at least:

a reservoir containing a composition P, in particular cosmetic or dermatological, to be applied to the keratinous material, an end fitting for the application of the composition contained in the reservoir, the end fitting comprising a plurality of application members and a distributor, the distributor comprising at least one storage cavity for the composition and supply orifices to conduct the composition from the storage cavity or cavities to the application members, a part at least of the application members does not lie above the cavity or cavities.

The cavity or cavities of the distributor do not extend under the entirety of the application members. The plurality of application members covers the cavity or cavities and protrudes around the cavity or cavities when the distributor is observed along a longitudinal axis of the end fitting.

Application Member

The device comprises several application members, in particular between two and eight, better between three and six, in particular in the form of balls. The multiplicity of application members facilitates a good distribution of the composition, in a continuous manner, and improves the ionization of the composition during treatment, if appropriate. The multiplicity of application members also makes it possible to improve the massaging effect in the course of the treatment.

At least one application member may be a ball, and better all the application members are balls.

At least some of the application members may be organized as a polygon, in particular as a triangle, and better all the application members are organized as a polygon, in particular as a triangle. Such a disposition facilitates the application and the treatment of zones which are difficult to access, for example the wings of the nose.

This configuration of the application members also facilitates good distribution of the composition over the whole of the application surface. Better homogeneity of the treatment is thus obtained. Safety and comfort related to good distribution of the electric current over the application surface is also improved, if appropriate. The disposition of the application members and the relatively high number thereof allow simultaneous application over a fairly large area.

The application members may be made of plastic or metal.

The application members are preferably neither electrically conducting, nor linked to the electrical supply circuit by metallic conductors.

The outer surface of an application member may be totally inert from a chemical point of view in relation to the composition applied and the keratinous material. The outer surface may be covered with a varnish. The outer surface may be polished. The outer surface may comprise a biocide material, if appropriate.

Moreover, the outer surface of an application member may be disposed in proximity to the composition reservoir, thereby making it possible to avoid the presence of specific ducts for transporting the composition from the reservoir to this outer surface.

The application members may be spherical or cylindrical, roller-shaped for example, or have some other shape, in particular ovoid.

Advantageously, at least one application member, better each application member, turns about at least one rotation axis. In an exemplary implementation of the invention, the outer surface of the application member exhibits a symmetry substantially of revolution about an axis of symmetry, the outer surface being able to be rotary about this axis of symmetry. As a variant, the application member may be rotary about a rotation axis distinct from this axis of symmetry.

The outer surface of an application member may exhibit any profile, in particular cylindrical or non-cylindrical, for example an ovoid or discoid shape.

In another exemplary implementation of the invention, the outer surface exhibits a substantially spherical shape. In particular, the application member is a ball. The latter may be all-axes rotary.

At least one application member may comprise a core on which an outer wall is attached. This may be the case for all the application members. This core may comprise a surface provided with reliefs and the outer wall may be able to deform during the application so as to come into contact with the reliefs. The latter make it possible to produce a massaging effect when the application member is in contact with the surface to be treated, and this may inter alia help the penetration of the composition into the skin and facilitate its action.

The outer wall may, as a variant, be rigid.

In an exemplary implementation of the invention, the outer wall comprises reliefs, which may comprise bumps or ribs.

Alternatively, at least one application member may comprise removable elements which afford the application member a relief. It is thus possible to change these elements with a view to modifying the dimensions of the application members, their surface properties, or else their roughness.

Advantageously, at least one application member is mounted in a removable manner on the device. All the application members may be mounted in a removable manner on the device.

The distributor may comprise a first face on which are made housings for the application members, in particular a housing for each of the application members. The first face may be plane, concave or convex. It is for example slightly domed.

The supply orifices are configured to conduct the composition from the cavity or cavities to the housings of the application members. The supply orifices may emerge in the housings elsewhere than in the bottom of the housings. This may make it possible to reduce the thickness of the distributor, so that the latter is more slender and less bulky.

Preferably, as mentioned hereinabove, a part at least of the housings of the application members does not lie above the cavity or cavities, in particular when the distributor is observed perpendicularly to the first face of the distributor. The cavity or cavities of the distributor do not then extend under the entirety of the housings of the application members. The plurality of housings covers the cavity or cavities and protrudes around the cavity or cavities when the distributor is observed perpendicularly to the first and second faces of the distributor.

The distributor comprises a second face opposite to the first, on which is made said at least one storage cavity for the composition. The cavity or cavities may be hollowed out with respect to the second face, which may be plane, concave or convex. The cavities may take the form of channels made in the distributor.

The distributor may comprise peripheral cavities, in particular three peripheral cavities, each of the peripheral cavities being able to enable the composition to be conveyed to several application members.

At least one peripheral cavity may be configured to convey the composition to two application members, for example two adjacent application members. In particular, each of the peripheral cavities may be configured to convey the composition to two application members, for example two adjacent application members. Thus, the application members may be linked pairwise by a corresponding cavity, which may be channel-shaped.

The supply orifices of the housings of the application members may emerge for this purpose in these peripheral cavities. Thus, the path followed by the composition may be minimized, thereby making it possible to reduce the volume of the cavity or cavities and thus the dead volume of composition present outside the reservoir and not yet dispensed.

The length of the path traversed by the composition in order to arrive at a given housing may be substantially equal to the length of the path traversed by the composition in order to arrive at another housing, to within 30%, better to within 20% or 10%, still better to within 5%. By "length of the path" is meant the shortest path made in the distributor between the point of arrival of the composition in the distributor and the point of arrival in the corresponding housing, when the device is in use.

It is thus possible to facilitate evenness of dispensing of the composition to the application members, and obtain a balanced supply flowrate of composition for each of the application members. "Balanced flowrate" is understood to mean that each of the application members receives a flowrate of composition which differs by less than 20% from the flowrate received by another application member, better by less than 10%, still better by less than 5%.

The shape of the distributor according to the invention facilitates good distribution of the composition to the application members, in spite of the high number thereof and of their different distance from the axis and from the exit orifice of the reservoir. It is thus possible to balance the dispensing of the composition on each application member while minimizing the quantity of composition stored in the distributor. The volume of the cavity or cavities may thus be reduced to the minimum.

The distributor may comprise at least one central cavity, in particular a single central cavity. This central cavity may be intended to be supplied directly with composition from the reservoir, in particular via the diffuser which will be described further on.

The peripheral cavities may be disposed as fins around the central cavity. The peripheral cavities may be supplied through v-shaped paths from the central cavity. The peripheral cavities may thus communicate with the central cavity through passages made at the periphery of the central cavity.

As a variant, the device is devoid of any central cavity, the peripheral cavities being mutually independent, and not being able to communicate with one another in the distributor. In this case, the peripheral cavities may be supplied with composition directly from the reservoir, in particular via the diffuser which will be described hereinafter.

At least one peripheral cavity, or indeed each of the peripheral cavities, may have a rectilinear channel shape, a supply orifice emerging at each of the ends of this channel. When they are three in number, these peripheral cavities may be disposed on each of the sides of a triangle starting from one of the vertices of said triangle, for example on half-sides of the triangle.

Each of the peripheral cavities may be supplied from the diffuser which will be described further on, the latter comprising a star-shaped diffuser cavity with three branches, each branch of the star supplying one of the peripheral cavities of the distributor in its middle or at one of its ends. The headloss undergone by the composition from its entry into the diffuser and up to the application members is preferably the same for each application member, at the very least differs by less than 20%, better less than 10%, or indeed less than 5%. Thus, one obtains an equivalent path traversed by the composition for the supply of each of the application members.

Diffuser

The device may comprise a diffuser directly in contact with the distributor, making it possible to feed the composition into the cavity or cavities of the distributor.

The distributor and the diffuser may each have a face in contact with the other of the distributor or of the diffuser. These faces may be plane. The surfaces of these faces may be tailored in such a way that there is in principle no composition that flows between the surfaces in contact. However, it is not possible to exclude the presence of a film of composition between these surfaces, without the clearance which accommodates this film constituting a cavity within the meaning of the invention.

The diffuser may comprise at least one metallic notch, for example three metallic notches making it possible to receive a metallic lug for electrical conduction, as explained further on. A first leaktight seal may be inserted between the diffuser and the distributor, in particular around the cavity or cavities of the latter. A second leaktight seal may also be provided under the diffuser, being held on the latter by a seal holding piece.

The device may comprise a cover configured to retain the application members in the housings of the distributor. The cover may comprise openings through which the application members protrude to the outside to allow the application of the composition.

Electrical Supply System

The device may comprise an electrical supply system for exposing the keratinous material to an electric treatment current in a zone of application of the composition.

By "electrical supply system" is meant an electrical assembly able to induce a potential difference between one or more electrodes and at least one counter-electrode. If the end fitting is placed on the person's face and if the counter-electrode is held in a hand, the potential difference is established between the person's face and their hand.

Electrically Conducting Distributor

The material or materials of the distributor may be chosen from the following list, which is not limiting: acetal, polyester, ABS, polyamide, polycarbonate, PP, PE, silicone, butyl, nitrile, viton, PBT, and combination of these materials. It may in particular be a plastic, for example polycarbonate preferentially.

The distributor may be electrically conductive. The material of the distributor may be rendered electrically conducting by inserting a filler, in particular into a polymer matrix, this filler being able to be chosen from the following list, which is not limiting: metal, graphite, fiber or carbon powder.

In one embodiment, the distributor is formed in at least one thermoplastic material, which comprises an electrically conducting filler, for example a carbon filler or a metallic filler. A carbon filler is preferred so as to ensure that the distributor is fairly lightweight.

In one embodiment, the cover is not electrically conducting.

In one embodiment, the cap is not electrically conducting.

The distributor may be electrically connected to the electrical supply system by a metallic lug. The latter may make it possible to ensure the transfer of the electric current from the electrical supply system to the distributor, when the latter is conducting. The distributor and the composition may be the only elements in the end fitting to be electrically conducting. In particular, the cap, the cover and/or the application members might not be electrically conducting. The only element in contact with the skin which may be electrically conducting is the composition.

Electrodes

The electrical supply system may comprise an electrode situated remotely from the keratinous material and in contact with the composition, and a counter-electrode, preferably coming into contact with the keratinous material in a zone not exposed to the composition.

According to the invention, by "electrode" is meant a positively charged (anode) or negatively charged (cathode) electrode. This electrode may be disposed in the application tip, so as to ensure the passage of the electric current into the composition. The electrode is then disposed inside the end fitting. In this case, it does not come directly into contact with the keratinous material, but with the composition itself. The composition may be the only conducting substance in contact with the skin during the use of the device. The electrode may not be in contact with the keratinous material, in particular the skin, the end fitting not comprising any electrically conducting material in contact with the skin.

Throughout the text, the term "electrode" signifies a single isolated electrode. An electrode may take for example the form of a ball, stud, tab. The device may comprise a single or several electrodes.

By "counter-electrode" is meant an electrode taken to a higher potential (cathode) or lower potential (anode) than the other electrode. The sign of the polarity of the counter-electrode is opposite to that of the electrode. In general, the latter is disposed on the body of the device or on a hand-piece. The counter-electrode is intended to come into contact with a bodily zone of the person undergoing the care. For example, it may be grasped between the person's fingers or between their palm and fingers. In one configuration, the counter-electrode is disposed on the end fitting. In this eventuality, it is separated from the electrode by an insulating space and is distanced as far as possible from the electrode so as to avoid any leakage current.

The electrode may be housed inside the end fitting, the electrode being in particular distanced from the outer wall of the application member by a distance of between 0.2 mm and 5 mm. This distance represents the gap between the electrode and the outer surface of the application member. This distance is the shortest measurable distance between the electrode and the outer surface of the application member. It is measured between any point of the electrode and of the outer surface of the application member, provided that the measured distance is the shortest distance.

Advantageously, the electrical supply system comprises a current generator suitable for controlling the intensity of the treatment current which flows between the electrode and the skin, thereby making it possible to control the voltage U between the electrode and the counter-electrode. The voltage U generated depends on the impedance of the "skin+composition" system. The voltage U is limited to a maximum value $U_{max}$ deliverable by the current generator, for safety reasons (about 100V for example). This voltage $U_{max}$ may be less than 150V.

The electrode may be plane, for example in the form of a plane disk or of a polygon. The electrode may be hollow, being formed for example by stamping or bending an electrically conductive metal sheet. The electrode may be porous.

Materials Able to be Used to Produce the Electrodes

The electrode may comprise:
- a metal, stainless steel for example,
- a noble metal (gold, titanium), inert with respect to the formula,
- a metal plated with a noble metal,
- an alloy,
- a composite, plastic material filled with carbon microfibers for example,
- a conductive woven fabric,
- a conductive nonwoven fabric,
- a polymer material rendered conductive,
- a fibrous material,
- conducting polymeric fibers, for example such as described in the publication CN101532190,
- carbon fibers, for example as described in the publication JP2009179915,
- silicones rendered conductive by the addition of conductive fillers such as silver, copper or carbon. Such silicones are supplied, for example, by the companies Saint-Gobain, Plastics Performance and Aquitaine Caoutchouc 2000,
- conductive metallic fabrics, supplied for example by the companies Utexbel and Cousin Biotech,
- carbon-loaded vinyl, supplied for example by the companies Copema and Rexam,
- electrosurgical plates, supplied for example by the companies Copema and 3M,
- intrinsic conducting polymers, supplied for example by the company Planiplast.

Electrical Parameters

The electrical energy source may comprise any cell or any accumulator. The voltage between the electrodes is for example between 1.2 V and 24 V, preferably between 1.2 and 3.3 V. If appropriate, the passage of the current may create pointlike heating.

At equivalent current density, the device may in particular deliver a current density, at the level of the skin, preferably of less than or equal to 0.500 mA/cm$^2$, for example of between 0.01 mA/cm$^2$ and 0.500 mA/cm$^2$, for example between 0.1 mA/cm$^2$ and 0.3 mA/cm$^2$.

Control and Warning System

The device may furthermore comprise a control system sensitive to the impedance of the skin. The control system may be configured to perform a measurement giving information on the impedance of the skin. By "measurement" is meant that the measured magnitude is compared with a threshold value, for example whether or not the measured magnitude has exceeded the threshold value, or whether or not the measured magnitude is situated in a given interval.

The device may furthermore comprise a warning facility providing the user with a signal in response to information originating from the control system sensitive to the impedance of the skin. The warning facility may thus make it possible to forewarn the user that the measured impedance has exceeded a threshold value.

The signal provided may in particular relate to the possible necessity to modify the current density between the electrodes and/or the quantity of composition to be dispensed. This modification may be performed automatically by a slaving system of the device, or else manually by the user. The signal may for example invite the user to dispense an additional dose of composition. The signal may as a variant or additionally invite the user to increase the current density.

The threshold value or values of the warning facility may be preprogrammed in the device, or else be fixed by the user, or else depend on the composition reservoir introduced into the device, if the reservoir is recognized by the device and if a corresponding threshold is automatically determined as a function of an identifier of the reservoir.

If there is insufficient composition between the electrode and the skin, the impedance is very high. The voltage U may become too high.

If the quantity of composition between the electrode and the skin increases, the voltage U may decrease because of a decrease in the impedance at this location.

The device may comprise a member for adjusting the current density flowing between the electrodes, in particular a manually actuatable member, and/or a device for automatically regulating the current density. The current density (A/cm$^2$) may be regulated so as to ensure the efficacy of the treatment and/or to limit painful sensations. The regulation of the density of the current may be performed manually by the user, the latter being able to modify the intensity of the current at will, or else when the warning facility signals to him that this is necessary, or automatically, by virtue of a system for slaving the current density.

The device may comprise a system for slaving the current density between the electrodes to the impedance measurement performed by the control system.

The warning facility may comprise one at least of a telltale light, of a sound warning facility, and of a vibratory warning facility, the warning facility preferably being triggered when the impedance measured by the control system lies in a predefined impedance range.

In a variant embodiment, the electric current between the electrodes is generated by a low-frequency current generator. In a variant embodiment, the electric current is not generated by a voltage generator.

The device may comprise an electronic timeout system configured to control the quantity of composition dispensed and/or the duration of the treatment.

Control Member

The device may comprise a control member for the dispensing of composition, in particular a push-button (for example an ON/OFF button) or a rotary thumbwheel, and/or a device for regulating the composition flowrate. The control member is configured to be actuated manually by the user. The control member may be configured to allow the dispensing of a dose of composition, or as a variant a continuous stream of the composition. In an exemplary embodiment, the dispensing of composition continues as long as the control member is engaged, for example as long as the push-button is depressed.

The user may trigger the dispensing of composition when the quantity of composition present is insufficient to ensure the efficacy of the treatment. Regulation of the quantity of composition may be performed manually by the user, the latter being able to modify the quantity of composition dispensed at will, or else when the warning facility signals to him that this is necessary, or automatically, by virtue of a system for slaving the quantity of composition dispensed to a measurement performed on the keratinous material.

The device may comprise a system for slaving the quantity of composition exiting the reservoir to the impedance measurement performed by the control system. The slaving of the dispensing of composition to the impedance of the skin makes it possible to ensure the presence of a sufficient quantity of cosmetic composition throughout the treatment. The quantity of composition may be adjusted automatically, as a function of the measurement performed.

The device may comprise a switch making it possible to place the device in automatic mode where the quantity of composition dispensed is slaved to the impedance measured by the control system or in semi-automatic mode where the warning facility advises the user on the need to modify the quantity of composition dispensed. By "semi-automatic mode" is meant that the warning facility may warn the user of the necessity to dispense composition manually. "Automatic mode" is understood to mean that the dispensing of composition is engaged automatically, as mentioned hereinabove, in case of necessity. In this case, the warning facility may not operate or as a variant may operate so as to signal to the user that some composition will be dispensed.

Reservoir

The mechanism for dispensing the formulation at the outlet of the reservoir may comprise a pump. Advantageously, the dispensing system comprises an air pump, so as to compress the air between the walls of the reservoir and its housing in the device. The walls of the reservoir are preferably flexible and the walls of the housing are preferably rigid.

More advantageously, the housing is airtight. The reservoir is compressed in a controlled manner by the air pump. This creates a certain pressure in the housing to regulate the flowrate of formula. A unidirectional valve at the end of the reservoir may make it possible to safeguard the formula from contact with the air.

When the current generator detects a dip in voltage, it may activate the pump so as to dispense the composition from the reservoir. The impedance is thus rebalanced. This principle makes it possible to guarantee a sufficient quantity of composition between the electrode and the skin. It makes it possible to optimize the penetration of the composition.

The reservoir may have a variable internal volume and comprise at least one wall that is elastically deformable so as to reduce the internal volume, in particular two elastically deformable walls opposite one another.

The reservoir may be designed to be mounted in a removable manner on the device such that, when the reservoir has been emptied, it can be replaced with another or removed in order to be filled, when the reservoir has a filling orifice.

Advantageously, the reservoir has an elastically deformable outer wall.

Preferably, the reservoir comprises an exit orifice emerging through a duct in the diffuser.

Advantageously, the reservoir is formed as a single component. It is preferably molded from a single piece, in particular from the same thermoplastic material, for example PEBD, PEHD, a mixture of PEBD and PEHD, PP, or a mixture of PE and PP in any proportion. The thickness of the wall of the reservoir is for example between 0.1 and 1 mm, and in the second zone between 0.3 and 0.8 mm.

Advantageously, the total internal volume of the reservoir is between 1 and 100 $cm^3$, preferably between 20 and 50 $cm^3$, in the rest configuration of the deformable zone. This volume is optimal for a few uses or a repeated treatment extending over a few weeks.

Preferably, the interior volume of the reservoir may shrink by a volume equal to between 10% and 50% of the interior volume of said reservoir in the rest configuration of the deformable zone. This variation in volume has the advantage of being visible and measurable.

The reservoir may be manufactured by injection blow molding or extrusion blow molding.

The reservoir may be removable. The reservoir may in particular be a single-use reservoir. It may or may not be a single-dose reservoir.

Composition

It is possible to use with the device at least one cosmetic or dermatological composition.

The composition(s) used may be in all forms, for example in the form of an aqueous solution, of an oil, of an emulsion, of a powder or of a gel. The composition(s) used may also be sprayed onto the skin.

When the composition(s) used is/are in the form of a gel, the latter can take on the shape of the electrode to which it is applied, as mentioned above.

The composition(s) may comprise an active principle.

Advantageously, the composition is chosen from among:
- a face care or body care composition, comprising in particular an active agent chosen from humectant or moisturizing active agents, anti-ageing active agents, for example depigmenting active agents, active agents that act on cutaneous microcirculation or seboregulating active agents,
- a composition for making up the face or body,
- a hair composition, in particular a composition for washing the hair, for hair care or conditioning, for temporary form retention or shaping of the hair, for the temporary, semi-permanent or permanent dyeing of the hair, or for relaxing or permanent-waving, in particular a composition for relaxing, dyeing or bleaching the roots and hair, and
- a composition for the scalp, in particular an antidandruff composition, a composition for preventing hair loss or for promoting regrowth of the hair, an anti-seborrheic, anti-inflammatory, anti-irritation or soothing composition, a mark-preventing composition or a composition for stimulating or protecting the scalp.

The device may be used in diverse cosmetic or dermatological treatments, for example to combat wrinkles, herpes, acne or to redensify the skin or the hair.

Complementary Functions

The device may furthermore comprise one at least of: a light source, a heat source, an infrared source or a resistance, this list not being limiting.

The device may comprise one or more treatment modules which may be activated selectively; for example it may be envisaged to subject the end fitting to light, to a heat source, or indeed to vibrations, as will be specified further on.

i) Light Source

According to the invention, the device advantageously comprises a light source.

The light source may be, for example, at least one LED, such as described in documents FR-A-2 917 299, US-A-2010/274329 or WO-A-2008/057640.

ii) Heat Source

According to the invention, the device advantageously comprises a heat source.

In this case, it is possible to modify the temperature of the external surface of the end fitting and/or of the treated region and/or to transmit energy to the external surface of the end fitting and/or to the treated region.

The device may for example comprise a heating resistance or a thermoelectric element or an infrared source positioned under the end fitting.

Preferably, the source of heat comprises an infrared source or a resistor.

The device may comprise a heating module, and be configured to heat the external surface of the end fitting to a predefined temperature for example to a temperature of between 35° C. and 45° C. In the case of a device comprising a heating module, the heating surface may reach a temperature of 10° C. to 35° C. higher than the ambient temperature, preferentially from 15° C. to 25° C. in heating mode. The power delivered by the heating module may be between 0.25 and 10 W, preferably between 0.5 and 5 W.

More preferably, the source of heat is housed entirely inside the device.

The resistor may be connected to a board by two insulated connectors, using for example the location of the breaker switches.

The infrared source may be integrated into the body of the device, as the handle. The external part of the device, for example a shell, may serve to guide the infrared radiation to the end fitting.

The electrical circuit may comprise at least one electronic breaker switch linked in series with the heating member and which makes it possible for example to supply it with the desired ratio.

BRIEF DESCRIPTION OF THE DRAWINGS

The invention will be better understood on reading the detailed description which will follow, of nonlimiting examples of implementation of the invention, and on examining the appended drawing in which.

DETAILED DESCRIPTION

Represented in FIGS. 1 to 9 is a device 1 in accordance with the invention. It comprises a body 12 on which is mounted an end fitting 2 comprising six application members 6 each having a ball shape, and a composition reservoir 3 housed inside the body 12, and represented dashed. The end fitting 2 is fixed by snap-fastening onto the body 12. It could be mounted in some other manner. In the example considered, the body 12 is made of thermoplastic material. As a variant, the latter may be made from any other material. Furthermore, the application members 6 are plastic balls. The application members 6 could have any other shape, being for example rollers.

The application members 6, six in number in the example described, are disposed as a triangle, thereby making it possible to facilitate the application and the treatment of zones that are difficult to access, for example the wings of the nose.

Figure 1:
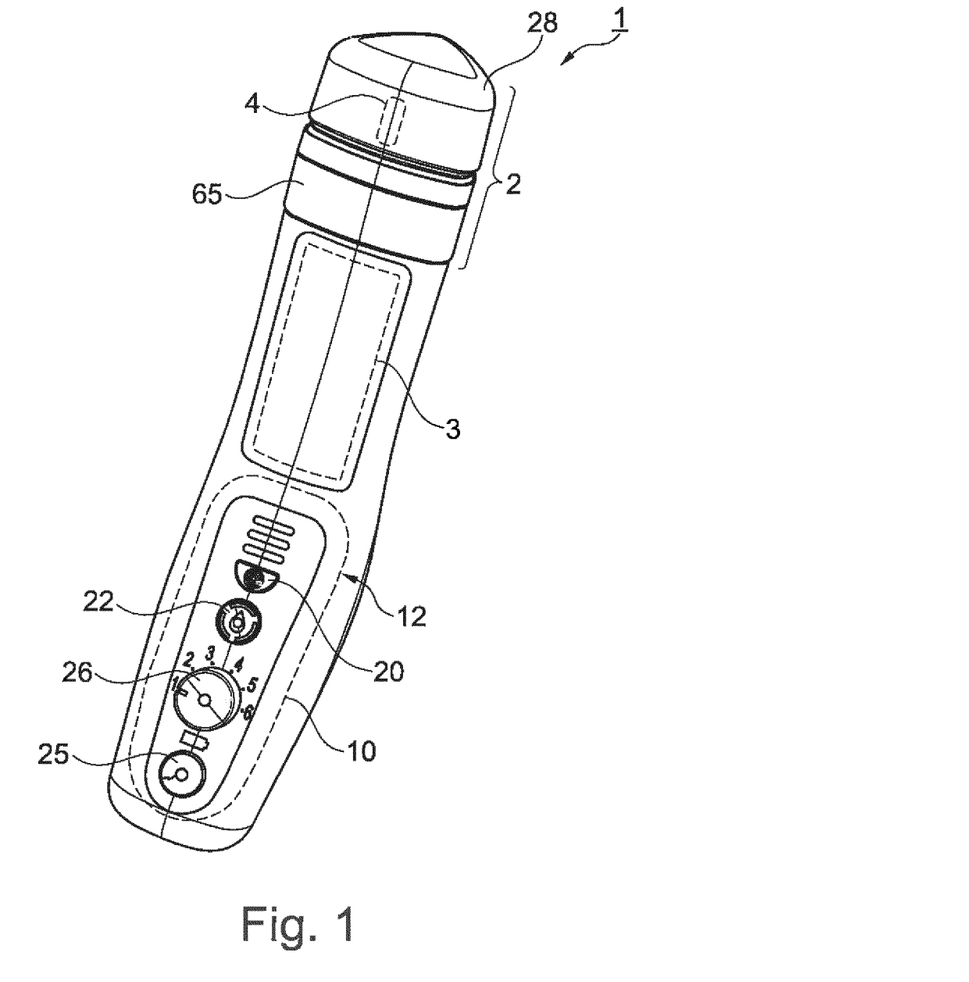
FIGS. 1, 2, 4 and 5 are schematic and partial views, in perspective, of a device in accordance with the invention.

The device 1 comprises an electrode 4 seen dashed in FIG. 1, the electrode 4 being housed inside the end fitting 2, as well as a counter-electrode 5 disposed on the body 12. The counter-electrode 5 is in contact with the hand of the user when the latter holds the device 1 in their hand, in such a way that the electrical circuit between the electrode 4 and the counter-electrode 5 closes by passing into the body of the user at the moment of treatment. The polarization of the electrode 4 and that of the counter-electrode 5 are reversible (+ or −) according to the nature of the composition used.

Figure 7A:
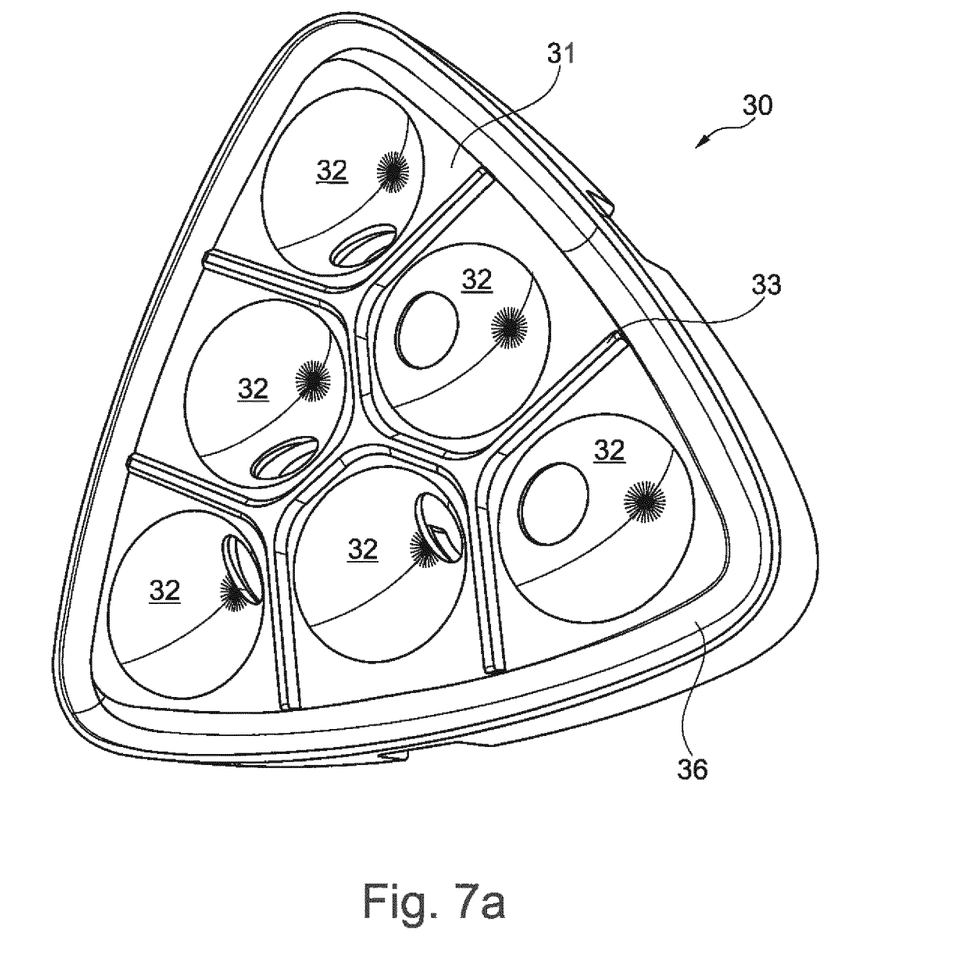
Figure 7B:
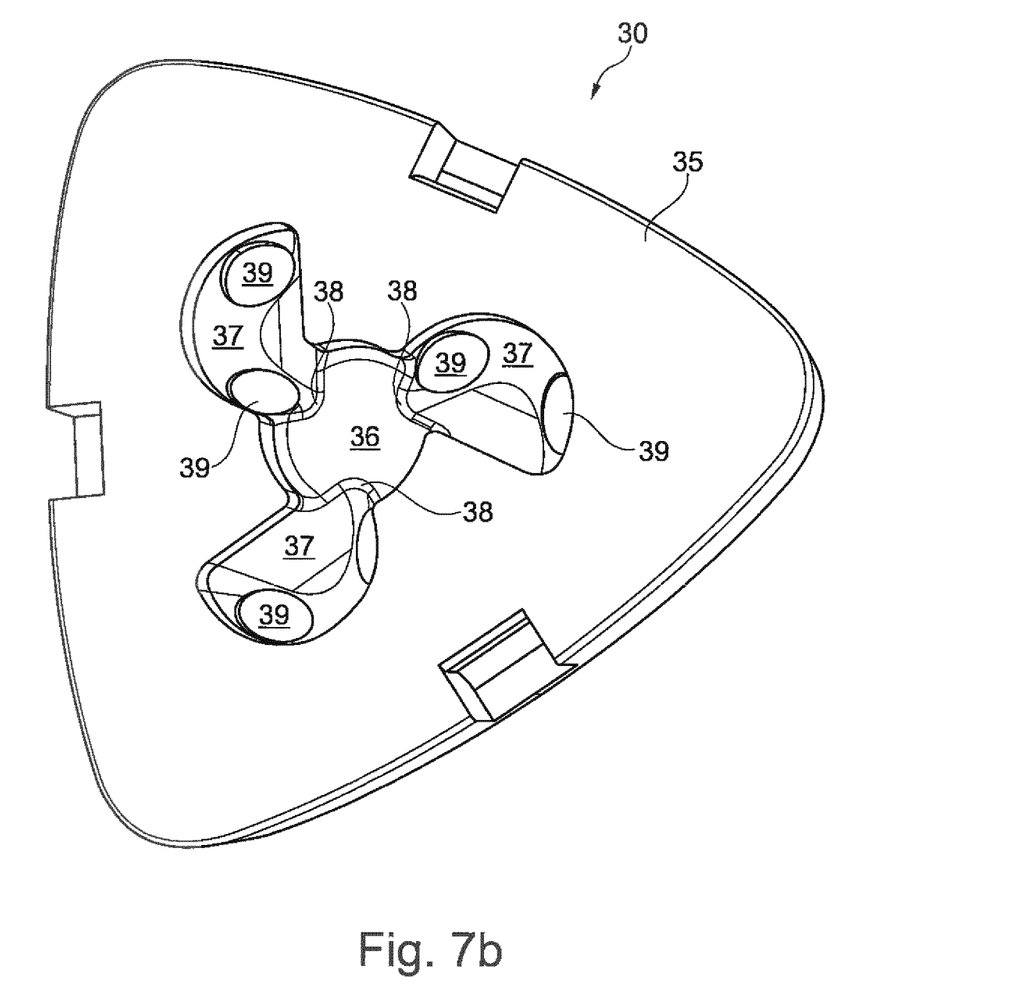

The electrode 4 is connected to a pole of an electrical supply system 10 housed in the body 12 and communicates with the composition when the latter passes into a distributor 30, illustrated in FIGS. 7a and 7b. The composition thereafter passes over the application members 6 and arrives at the application surface, the skin in the example described, with a view to treatment. The counter-electrode 5 is connected to the other pole of the electrical supply system 10, which is supplied by a battery (cells or rechargeable battery).

To begin the treatment, the user turns on the device by means of a push-button 25. An electric current then begins to flow between the electrode 4 and the counter-electrode 5, when the apparatus is applied to the person's face for example, at the same time as the composition is dispensed automatically or by action of the user on a control member 22.

In a variant embodiment, the intensity of the current may be adjusted by the user by virtue of an adjustment member 26 for adjusting the current density between the electrodes, which is a graduated rotary button in the example of FIG. 1.

If there is insufficient composition between the electrode 4 and the skin, the impedance of the skin increases. The device comprises a control system sensitive to the impedance of the skin, configured to detect such a variation in the impedance. The device also comprises a warning facility 20 making it possible to provide the user with a signal as a function of information originating from the control system. In the example described, the warning facility 20 provides a luminous signal. The user may then dispense an additional dose of composition by pressing the composition dispensing control member 22, which is a push-button in the example of FIG. 1.

The structure of the end fitting 2 will now be described in greater detail with reference to FIGS. 2 to 9.

Figures 2, 3:
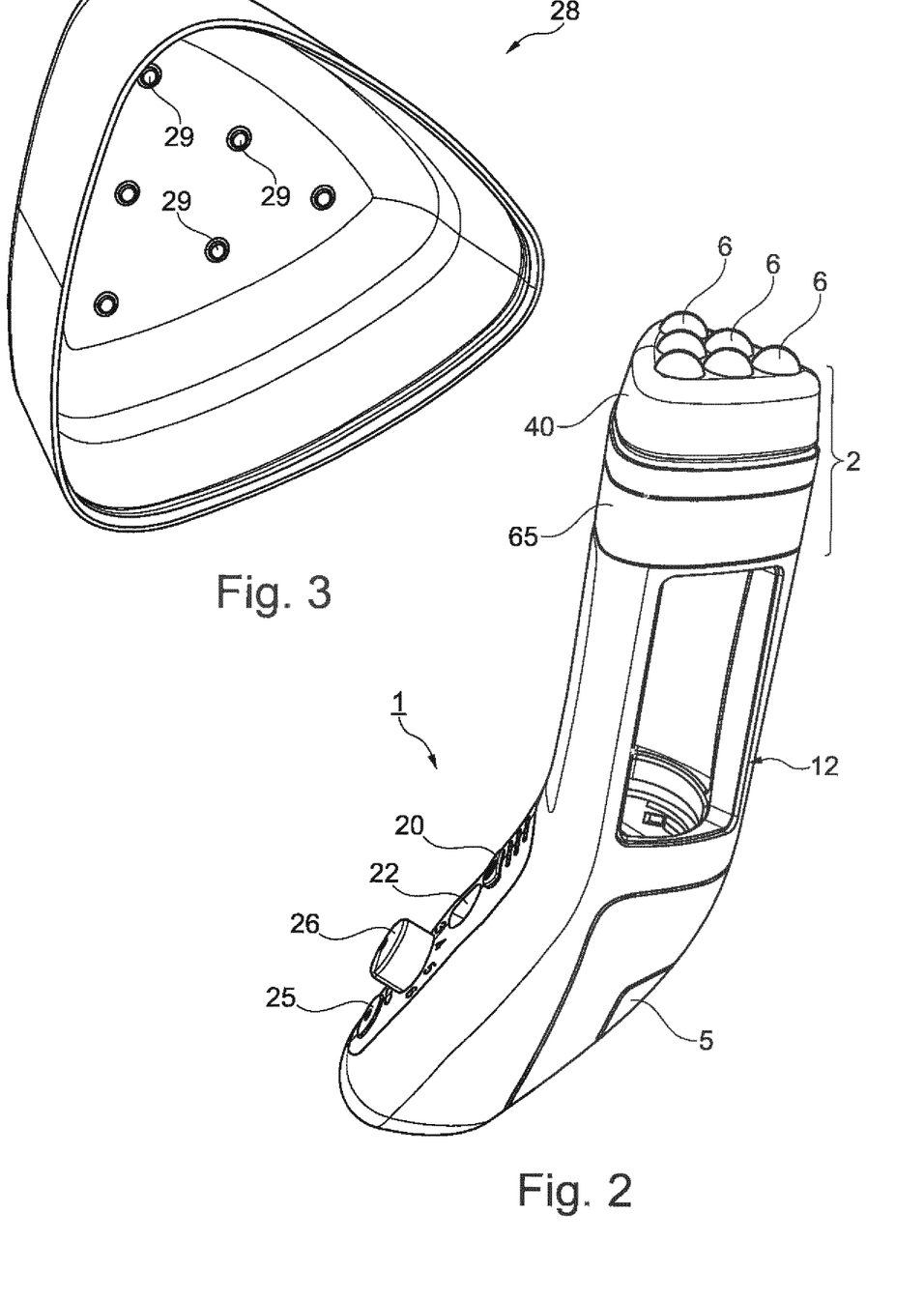
FIG. 3 is a schematic and partial view, in perspective, of the cap for closing the device of FIG. 1, FIGS. 6a and 6b are schematic and partial views, in perspective, of the cover of the device of FIG. 1, FIGS. 7a and 7b are schematic and partial views, in perspective, of the distributor of the device of FIG. 1, FIGS. 8a and 8b are schematic and partial views, in perspective, of the diffuser of the device of FIG. 1.

The end fitting comprises firstly a closure cap 28, illustrated in isolation in FIG. 3, which is configured to be fixed by snap-fastening onto the remainder of the device, and more particularly onto a cover 40 which will be described hereinafter. The closure cap 28 comprises, in the bottom thereof, reliefs 29 for setting the application members 6. This closure cap is preferably not electrically conducting.

Figure 6A:
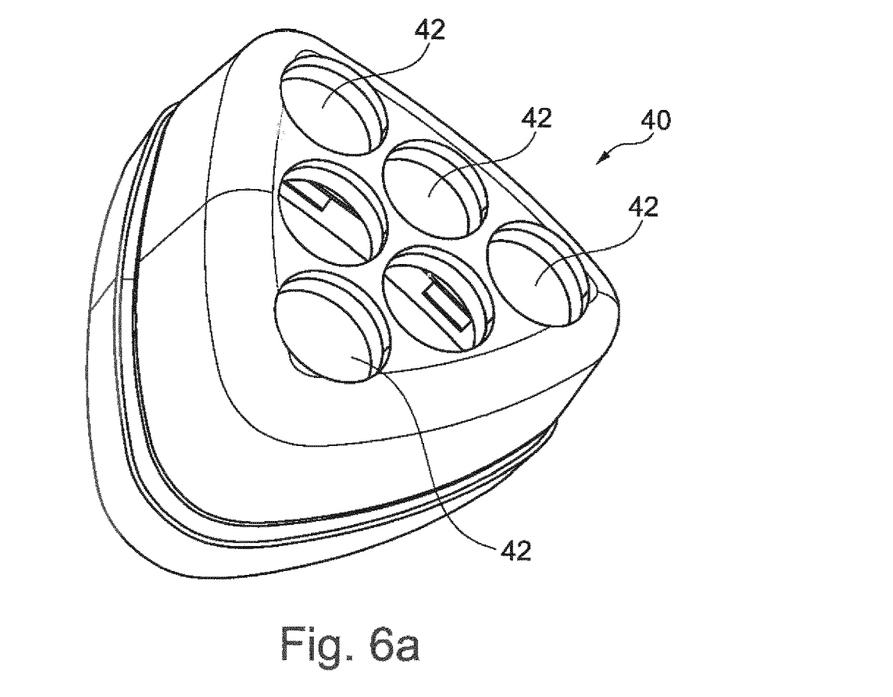
Figure 6B:
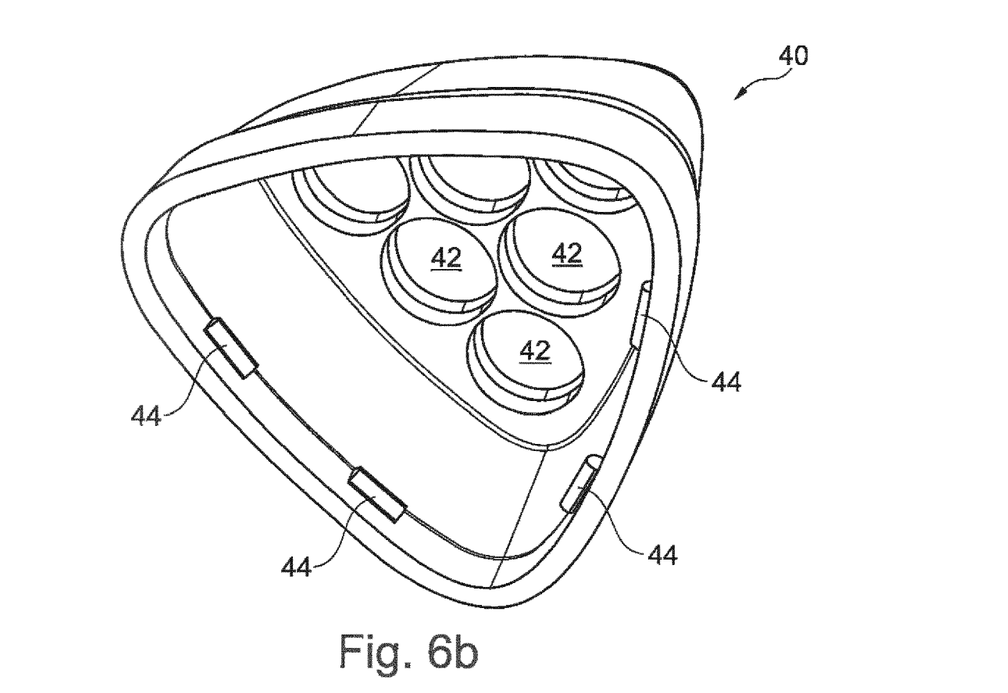

The cover 40, illustrated in isolation in FIGS. 6a and 6b, makes it possible to retain the application members 6 in place. The cover 40 comprises openings 42 through which the application members 6 protrude to the outside to allow the application of the composition, as may be seen in FIG. 2. The cover 40 is fixed by means of lugs 44 on the diffuser 50 which will be described hereinafter.

Figure 4:
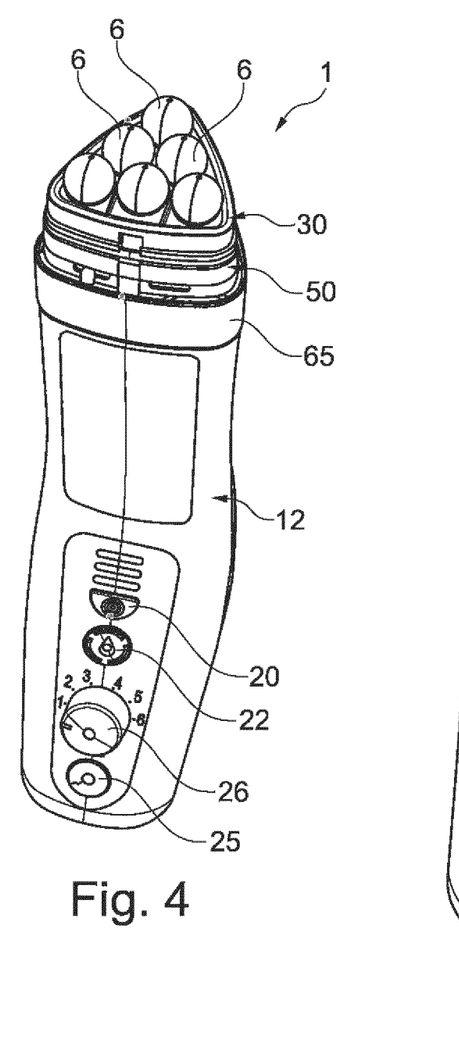
Figure 5:
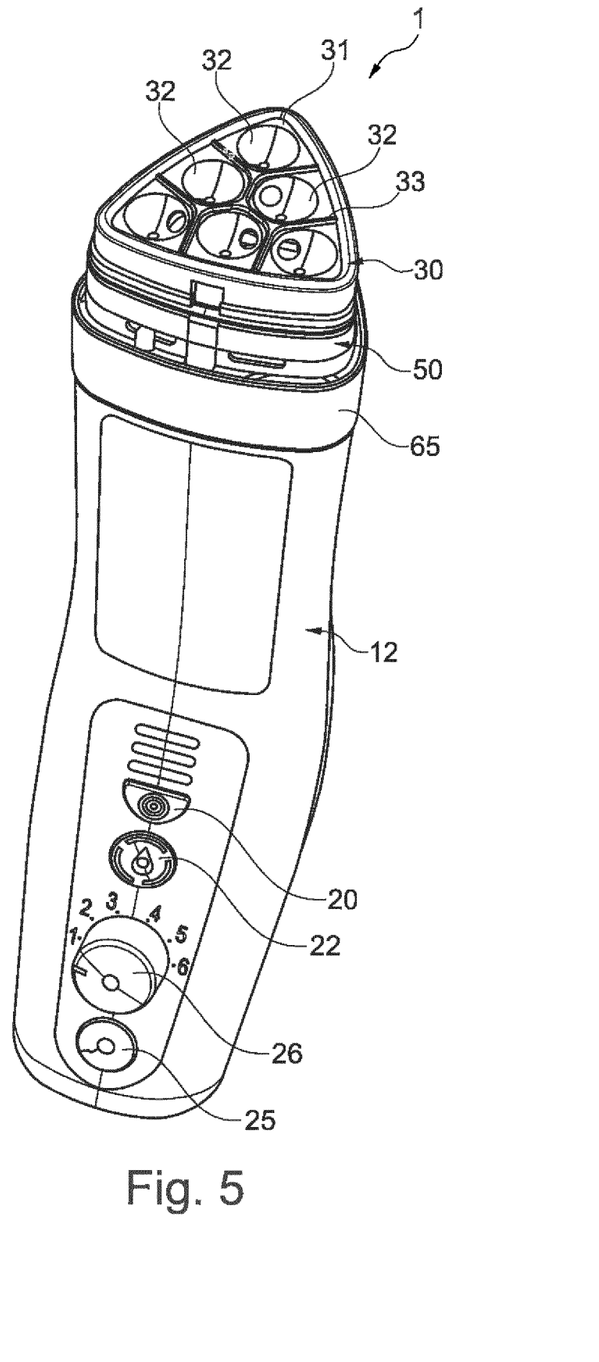

The end fitting 2 further comprises a distributor 30 disposed under the cover 40, which receives the plurality of application members 6, as illustrated in FIGS. 4 and 5. The distributor is illustrated in isolation in FIGS. 7a and 7b.

The distributor is electrically conducting, being formed from a thermoplastic material comprising an electrically conducting filler, in particular a carbon filler or a metallic filler.

The distributor is connected electrically to the electrical supply system 10 by a metallic lug 54. This metallic lug 54 makes it possible to ensure the transfer of the electric current from the electrical supply system 10 to the distributor and then to the composition. The distributor and the composition are the only elements in the end fitting to be electrically conducting.

The distributor 30 comprises a first face 31 on which are made housings 32 for the application members 6, in particular a housing 32 for each of the six application members 6. The first face 31 also comprises a rib 33 with several branches, separating the housings 32 from one another.

The distributor 30 comprises a second face 35 opposite to the first face 31, on which is made at least one storage cavity for the composition. In the example described, the distributor 30 comprises a central cavity 36 and three peripheral cavities 37, each of the peripheral cavities 37 being able to make it possible to convey the composition to two of the application members.

The peripheral cavities 37 are disposed like fins around the central cavity 36. The peripheral cavities 37 are supplied with composition from the central cavity 36. They communicate with the central cavity 36 through openings 38 made at the periphery of the central cavity 36. The central cavity is intended to be supplied directly with composition from the reservoir 3, in particular by the diffuser 50 which will be described further on.

Each peripheral cavity 37 is configured to convey the composition to two adjacent application members 6. For this purpose the distributor comprises supply orifices 39 to conduct the composition from the peripheral cavities 37 to the application members 6, more particularly to the housings of the application members. The supply orifices 39 of the housings of the application members emerge for this purpose in these peripheral cavities 37 and in the housings 32.

The cavities 36 and 37 are hollowed out with respect to the second face 35, which is plane in this example.

A part at least of the housings 32 of the application members 6 as well as a part at least of the application members 6 do not lie above the cavities 36 and 37, when the distributor 30 is observed perpendicularly to the first face 31 of the distributor. The cavities 36 and 37 of the distributor do not extend under the entirety of the housings 32 of the application members 6. The plurality of housings covers the cavities 36 and 37 and protrudes around the cavities 36 and 37 when the distributor is observed perpendicularly to the first face 31 of the distributor 30.

Figure 8A:
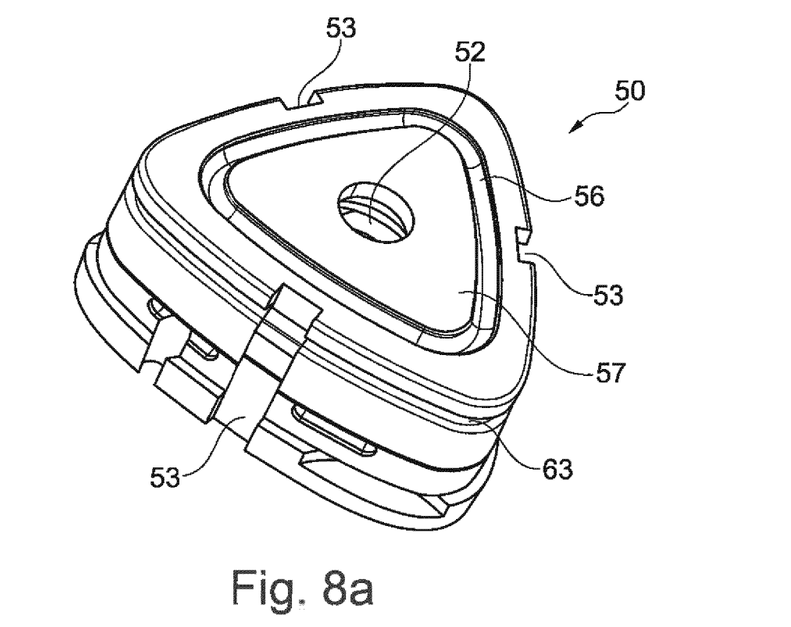
Figure 8B:
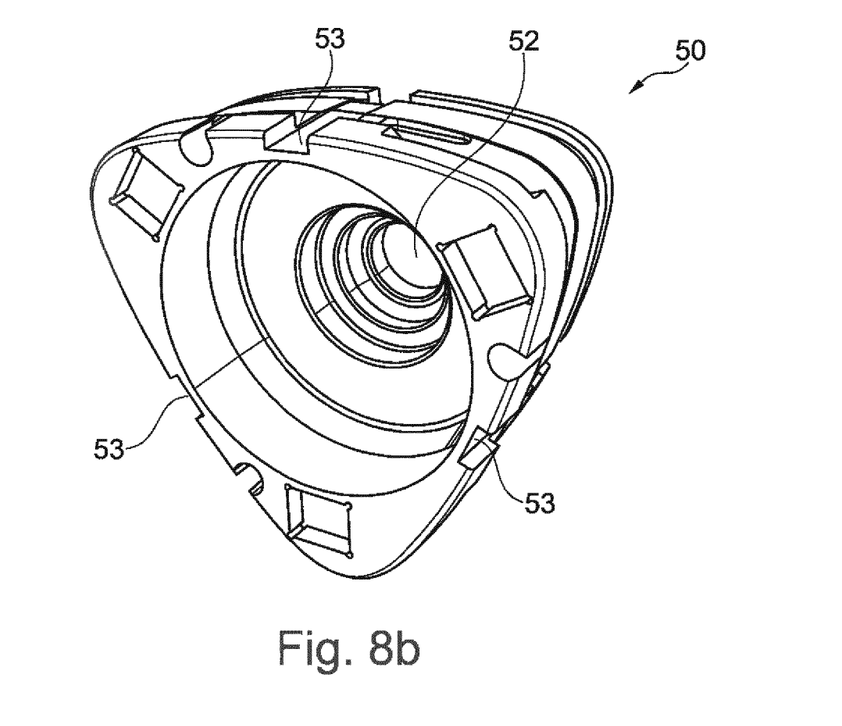

The end fitting 2 also comprises a diffuser 50 directly in contact with the distributor 30, making it possible to feed the composition into the cavities 36 and 37 of the distributor. The diffuser 50 comprises for this purpose a cavity 52 which is in the example described of circular general shape, supplying the central cavity 36. The composition thereafter passes through the openings 38 in the peripheral cavities 37, and then through the supply orifices 39 to the housings 32 of the application members 6, so as to be applied to the skin for example.

The diffuser 50 comprises three metallic notches 53 each making it possible to receive a metallic lug 54 for holding the distributor on the diffuser and electrical conduction.

Figure 9:
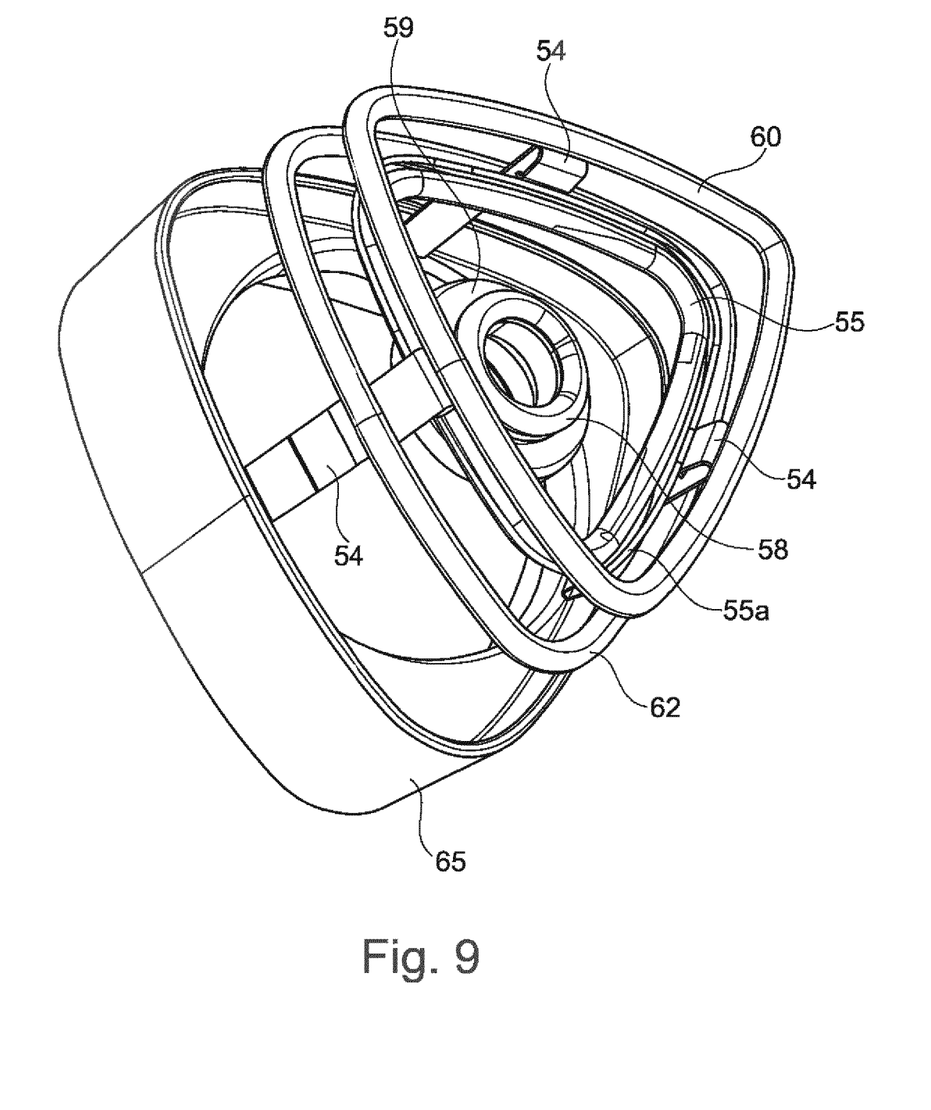
FIG. 9 is an exploded view of the other pieces forming the end fitting of the device of FIG. 1, and FIGS. 10a and 10b are schematic and partial views, in perspective, of a variant embodiment.

The end fitting further comprises a plurality of seals so as to ensure the leaktightness of the assemblage of the various pieces of which it is composed, and which have just been described. It comprises in particular, as illustrated in FIG. 9, a first leaktight seal 55 inserted between the diffuser 50 and the distributor 30, around the cavities of the latter, being set in a throat 56 of the diffuser made for this purpose on the upper face 57 thereof. This upper face 57 is intended to come into tight contact with the second face 35 of the distributor 30. A seal 55a surrounding the seal 55 may also supplement the leaktightness at this level.

A second leaktightness seal 58 may also be provided under the diffuser, at the level of the cavity of the diffuser 52, being held on the latter by a holding piece 59.

An upper seal 60 is provided on the distributor 30, around the housings 32 of the latter, and is housed in a peripheral throat 36 of the distributor 30.

An upper seal 62 for the diffuser is also provided, which is housed in a peripheral throat 63 of the diffuser 50, between the latter and an upper ring 65 of the body 12.

Figure 10A:
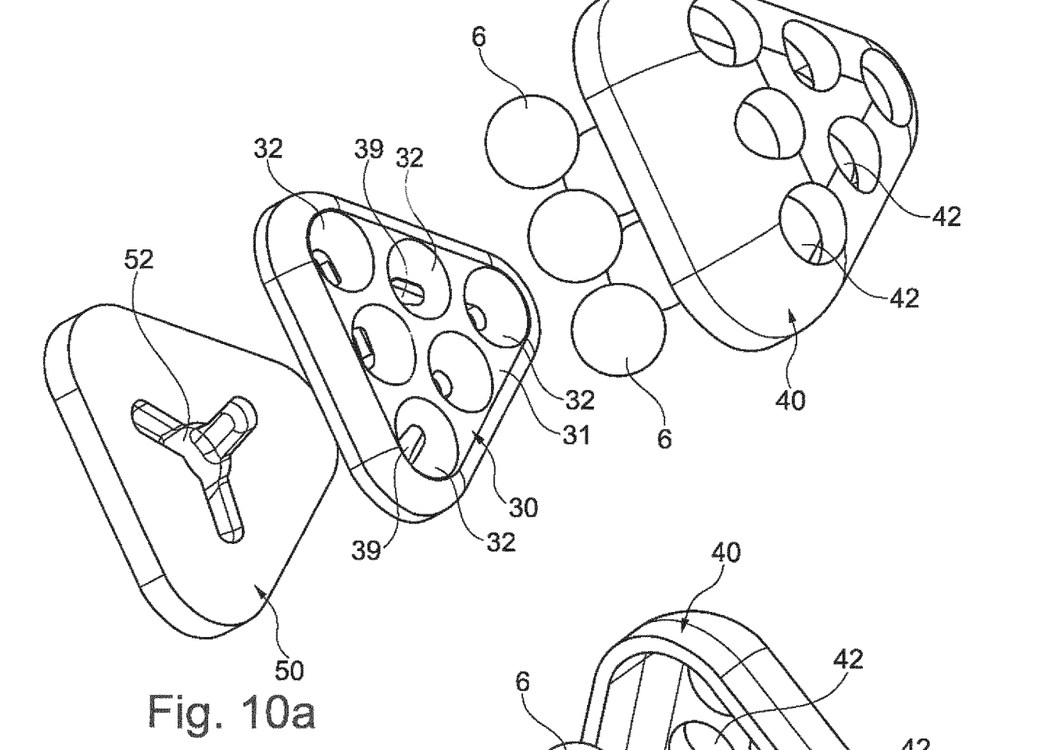
Figure 10B:
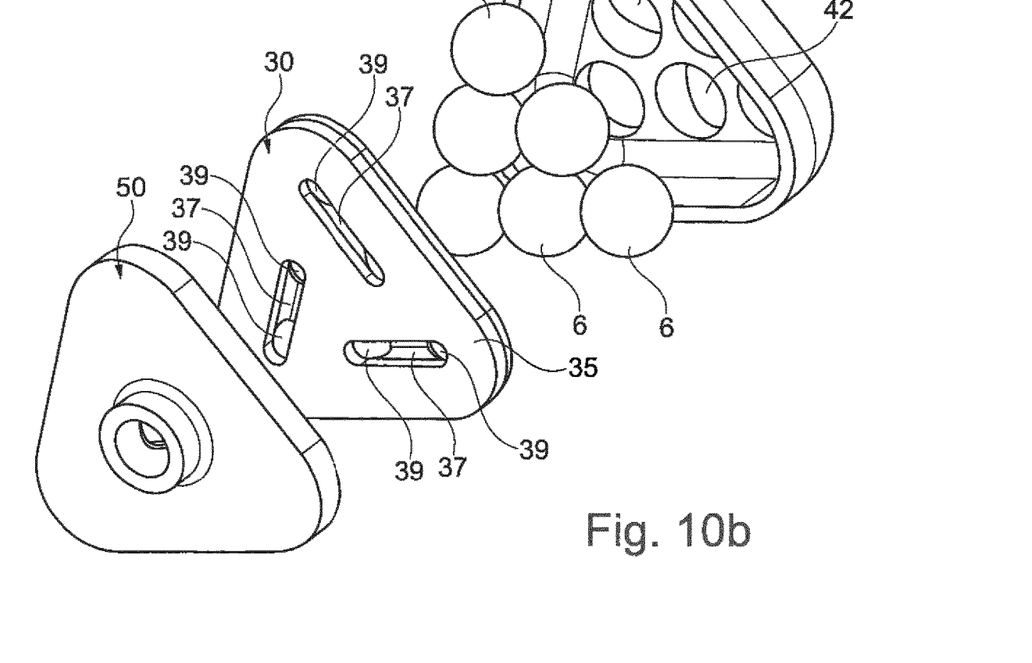

In the variant embodiment illustrated in FIGS. 10a and 10b, the device is devoid of a central cavity, the peripheral cavities 37 being mutually independent, and not being able to communicate with one another in the distributor 30. The peripheral cavities 37 are supplied with composition directly from the reservoir, by the diffuser 50. The latter comprises for this purpose a star-shaped cavity 52 with three branches, each branch of the star supplying one of the peripheral cavities 37 of the distributor 30, for example in the middle thereof. Thus, one obtains an equivalent headloss for the supply of each of the application members.

The peripheral cavities 37 have shapes of channels, a supply orifice 39 emerging at each of their ends. These peripheral cavities 37 are disposed on each of the sides of a triangle starting from one of the vertices of said triangle, for example on half-sides of said triangle, as illustrated.

The invention claimed is:

1. A device for treating human keratinous material, with the aid of an electric current, comprising:
   a reservoir containing a composition to be applied to the keratinous material, and
   an end fitting for the application of the composition contained in the reservoir, the end fitting comprising a plurality of application members and a distributor, the distributor comprising at least two storage cavities for the composition and supply orifices to conduct the composition from the storage cavities to the application members, the supply orifices are angled relative to one another along a longitudinal axis of the device, have angled flow paths relative to one another, and are configured to dispense the composition onto outer surface of the application members internally within the device;

the distributor being configured so that the flow rate of the composition arriving at the application members is identical to within 20% for at least two application members, wherein portions of the storage cavities that are directly connected to the supply orifices are laterally offset relative to and do not lie directly below a bottom of each application member along the longitudinal axis of the device, and the device comprising an electrical supply system for exposing the keratinous material to an electrical treatment current in a zone of application of the composition, the distributor comprising two opposite sides, a first side on which are made housings for the application members, and a second side on which is made said at least two storage cavities for the composition.

2. The device as claimed in claim 1, in which the distributor is configured such that the length of the path traversed by the composition in order to arrive at a given housing of an application member is substantially equal to the length of the path traversed by the composition in order to arrive at another housing of an application member, to within 30%.

3. A device for treating human keratinous material, with the aid of an electric current, comprising at least:

a reservoir containing a composition, to be applied to the keratinous material, and an end fitting for the application of the composition contained in the reservoir, the end fitting comprising a plurality of application members and a distributor, the distributor comprising at least two storage cavities for the composition and supply orifices to conduct the composition from the storage cavities to the application members, the supply orifices are angled relative to one another along a longitudinal axis of the device, have angled flow paths relative to one another, and are configured to dispense the composition onto an outer surface of the application members internally within the device;

the distributor being configured so that the flow rate of the composition arriving at the application members is identical to within 20% for at least two application members in which at least two supply orifices have different transversal cross sections, and the device comprising an electrical supply system for exposing the keratinous material to an electrical treatment current in a zone of application of the composition.

4. The device as claimed in claim 1, comprising several application members.

5. The device as claimed in claim 1, in which at least one application member is a ball.

6. The device as claimed in claim 1, in which at least some of the application members are organized as a polygon.

7. The device as claimed in claim 1, the distributor comprising a first face on which are made housings for the application members.

8. The device as claimed in claim 1, the distributor comprising peripheral cavities, each of the peripheral cavities being able to enable the composition to be conveyed to several application members.

9. The device as claimed in claim 8, in which at least one peripheral cavity is configured to convey the composition to two application members.

10. The device as claimed in claim 1, the distributor comprising at least one central cavity.

11. The device as claimed in claim 1, in which at least one peripheral cavity has a rectilinear channel shape, a supply orifice emerging at each of their ends.

12. The device as claimed in claim 1, comprising a diffuser directly in contact with the distributor, making it possible to feed the composition into the cavity or cavities of the distributor.

13. The device as claimed in claim 2, comprising a cover configured to be able to retain the application members in the housings of the distributor, the cover comprising openings through which the application members can protrude to the outside to allow the application of the composition.

14. The device as claimed in claim 1, in which the distributor is electrically connected to the electrical supply system.

15. The device as claimed in claim 1, in which the distributor is one-piece.

16. The device as claimed in claim 1, wherein the application members are not internally traversed by the composition.

17. The device as claimed in claim 1, wherein the application members are free in the housings.

* * * * *